(12) United States Patent
Yang et al.

(10) Patent No.: US 11,116,447 B2
(45) Date of Patent: *Sep. 14, 2021

(54) MODULAR WEARABLE SENSOR DEVICE

(71) Applicant: Vital Connect, Inc., Campbell, CA (US)

(72) Inventors: Yun Yang, Los Altos, CA (US); Azin Sahabi, San Francisco, CA (US)

(73) Assignee: Vital Connect, Inc., San Jose, CA (US)

(*) Notice: Subject to any disclaimer, the term of this patent is extended or adjusted under 35 U.S.C. 154(b) by 1176 days.

This patent is subject to a terminal disclaimer.

(21) Appl. No.: 15/063,393

(22) Filed: Mar. 7, 2016

(65) Prior Publication Data

US 2016/0183875 A1 Jun. 30, 2016

Related U.S. Application Data

(63) Continuation of application No. 13/480,212, filed on May 24, 2012, now Pat. No. 9,277,864.

(51) Int. Cl.
*A61B 5/00* (2006.01)
*A61B 5/0205* (2006.01)
(Continued)

(52) U.S. Cl.
CPC ............... *A61B 5/6833* (2013.01); *A61B 5/00* (2013.01); *A61B 5/02055* (2013.01); *A61B 5/05* (2013.01);
(Continued)

(58) Field of Classification Search
CPC ....... A61B 5/04; A61B 5/0402; A61B 5/0408; A61B 5/04085; A61B 5/04087;
(Continued)

(56) References Cited

U.S. PATENT DOCUMENTS 4,121,573 A 10/1978 Crovella et al.
4,762,497 A 8/1988 Burvee
(Continued)

FOREIGN PATENT DOCUMENTS

| WO | 1999/59225 | 11/1999 |
| WO | 2007/114591 | 10/2007 |
| WO | 2012/011780 | 1/2012 |

OTHER PUBLICATIONS

International Search Report and Written Opinion from International Application No. PCT/US13/42292 dated Aug. 30, 2013.

*Primary Examiner* — Eun Hwa Kim
(74) *Attorney, Agent, or Firm* — Brundidge & Stanger, P.C.

(57) ABSTRACT

A wearable sensor and method for providing a wearable sensor are disclosed. In a first aspect, the wearable sensor comprises a first module, wherein the first module comprises a top layer, a printed circuit board (PCB) layer, and a bottom layer. The bottom layer comprises a double adhesive layer that adheres to both the PCB layer and the user. The bottom layer includes at least two openings to house at least two electrodes for monitoring of a user. The wearable sensor further comprises a second module coupled to the first module, wherein the first module is disposable and the second module is reusable. In a second aspect, the method comprises providing the aforementioned wearable sensor.

19 Claims, 7 Drawing Sheets

(51) Int. Cl.
*A61B 5/05* (2021.01)
*A61B 5/08* (2006.01)
*A61B 5/259* (2021.01)
*A61B 5/332* (2021.01)

(52) U.S. Cl.
CPC .......... *A61B 5/0002* (2013.01); *A61B 5/0006* (2013.01); *A61B 5/0008* (2013.01); *A61B 5/0809* (2013.01); *A61B 5/259* (2021.01); *A61B 5/332* (2021.01); *A61B 2560/0214* (2013.01); *A61B 2560/0285* (2013.01); *A61B 2560/045* (2013.01); *A61B 2560/0412* (2013.01); *A61B 2560/0443* (2013.01); *A61B 2562/028* (2013.01); *A61B 2562/0271* (2013.01); *A61B 2562/12* (2013.01); *A61B 2562/125* (2013.01); *A61B 2562/164* (2013.01)

(58) Field of Classification Search
CPC ... A61B 5/0492; A61B 5/6801; A61B 5/6832; A61B 5/6833; A61B 2560/0412; A61B 2560/0443; A61B 2560/045; A61B 2562/12; A61B 2562/125; A61B 2562/227
See application file for complete search history.

(56) References Cited

U.S. PATENT DOCUMENTS

| | | |
|---|---|---|
| 5,500,635 A | 3/1996 | Mott |
| 5,749,365 A | 5/1998 | Magill |
| 6,161,036 A | 12/2000 | Matsumura et al. |
| 7,722,249 B2 | 5/2010 | Kim |
| 7,748,995 B1 | 7/2010 | Lee |
| 8,116,841 B2 | 2/2012 | Bly et al. |
| 9,277,864 B2 * | 3/2016 | Yang ................ A61B 5/00 |
| 10,327,660 B2 * | 6/2019 | Gallego ............ A61B 5/04325 |
| 2002/0180605 A1 | 12/2002 | Ozguz et al. |
| 2003/0050537 A1 | 3/2003 | Wessel |
| 2003/0149349 A1 | 8/2003 | Jensen |
| 2007/0270678 A1 | 11/2007 | Fadam |
| 2008/0091089 A1 * | 4/2008 | Guillory ............ A61B 5/4094 600/301 |
| 2008/0139953 A1 * | 6/2008 | Baker ................ A61B 5/0006 600/509 |
| 2008/0275327 A1 * | 11/2008 | Faarbaek ............ A61B 5/0002 600/382 |
| 2008/0287747 A1 | 11/2008 | Mestrovic et al. |
| 2009/0154523 A1 * | 6/2009 | Kim .................... G01K 1/024 374/141 |
| 2009/0171163 A1 | 7/2009 | Mates et al. |
| 2010/0081913 A1 | 4/2010 | Cross et al. |
| 2010/0160762 A1 | 6/2010 | McLaughlin et al. |
| 2011/0009729 A1 | 1/2011 | Shin et al. |
| 2011/0144470 A1 * | 6/2011 | Mazar ................ A61B 5/04085 600/391 |
| 2011/0237924 A1 * | 9/2011 | McGusty ............ A61B 5/0006 600/391 |
| 2013/0116533 A1 * | 5/2013 | Lian .................... A61B 5/0006 600/391 |
| 2013/0116534 A1 | 5/2013 | Woo |
| 2013/0213147 A1 | 8/2013 | Rice et al. |
| 2014/0031663 A1 * | 1/2014 | Gallego ............ A61B 5/04085 600/386 |
| 2014/0206976 A1 | 7/2014 | Thompson et al. |
| 2014/0206977 A1 | 7/2014 | Bahney et al. |
| 2014/0275932 A1 * | 9/2014 | Zadig ................ A61B 5/6833 600/391 |

\* cited by examiner

MODULAR WEARABLE SENSOR DEVICE

CROSS-REFERENCE TO RELATED APPLICATION

Under 35 U.S.C. 120, this application is a Continuation Application and claims priority to U.S. application Ser. No. 13/480,212, filed May 24, 2012, entitled "MODULAR WEARABLE SENSOR DEVICE," which is incorporated herein by reference in its entirety.

FIELD OF THE INVENTION

The present invention relates to wireless sensor devices, and more particularly, to a modular wearable sensor.

BACKGROUND

Sensor devices are used in a variety of applications including the health monitoring of users. In many of these health monitoring applications, a wireless sensor device is attached directly to the user's skin to measure certain data. This measured data can then be utilized for a variety of health related applications including but not limited to detecting whether the user has fallen, has suffered a heart attack, has difficulty breathing.

Utilizing these sensor devices, a user's health can be monitored continuously. However, due to the continuous nature of the monitoring, these sensor devices experience repeated use and high wear and tear. As a result, conventional sensor devices must often be replaced regularly to meet the high demands of monitoring a user's health around the clock. Due to the high replacement costs of these sensor devices, monitoring a user's health can become very costly.

These issues limit the usage of sensor devices to continuously measure a user's health. Therefore, there is a strong need for a cost-effective solution that overcomes the above issues by creating a decoupling sensor device that includes both a reusable and a disposable portion. The present invention addresses such a need.

SUMMARY OF THE INVENTION

A wearable sensor and method for providing a wearable sensor are disclosed. In a first aspect, the wearable sensor comprises a first module, wherein the first module comprises a top layer, a printed circuit board (PCB) layer, and a bottom layer. The bottom layer comprises a double adhesive layer that adheres to both the PCB layer and the user. The bottom layer includes at least two openings to house at least two electrodes for monitoring of a user. The wearable sensor further comprises a second module coupled to the first module, wherein the first module is disposable and the second module is reusable.

In a second aspect, the method comprises providing a first module, wherein the first module comprises a top layer, a printed circuit board (PCB) layer, and a bottom layer. The bottom layer comprises a double adhesive layer that adheres to both the PCB layer and the user. The bottom layer includes at least two openings to house at least two electrodes for monitoring of a user. The method further comprises coupling a second module to the first module, wherein the first module is disposable and the second module is reusable.

BRIEF DESCRIPTION OF THE DRAWINGS

The accompanying figures illustrate several embodiments of the invention and, together with the description, serve to explain the principles of the invention. One of ordinary skill in the art will recognize that the particular embodiments illustrated in the figures are merely exemplary, and are not intended to limit the scope of the present invention.

DETAILED DESCRIPTION OF PREFERRED EMBODIMENTS

The present invention relates to wireless sensor devices, and more particularly, to a modular wearable sensor. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

A modular wearable sensor device provides a cost-effective health monitoring sensor device. By implementing a reusable module and a disposable module that each decouple from each other and each comprise varying components, the modular wearable sensor device can be utilized to more efficiently and continuously monitor a user's health. One of ordinary skill in the art readily recognizes that the shape and placement of the components of both the reusable module and the disposable module can vary and that would be within the spirit and scope of the present invention.

To describe the features of the present invention in more detail, refer now to the following description in conjunction with the accompanying Figures.

In one embodiment, the modular wearable sensor device is a wireless sensor device in a "patch" form factor that is attached to the user for health monitoring. One of ordinary skill in the art readily recognizes that a variety of wireless sensor devices and form factors can be utilized including but not limited to a wireless sensor device that looks like a band-aid and adheres to the user's body and that would be within the spirit and scope of the present invention.

Figure 1:
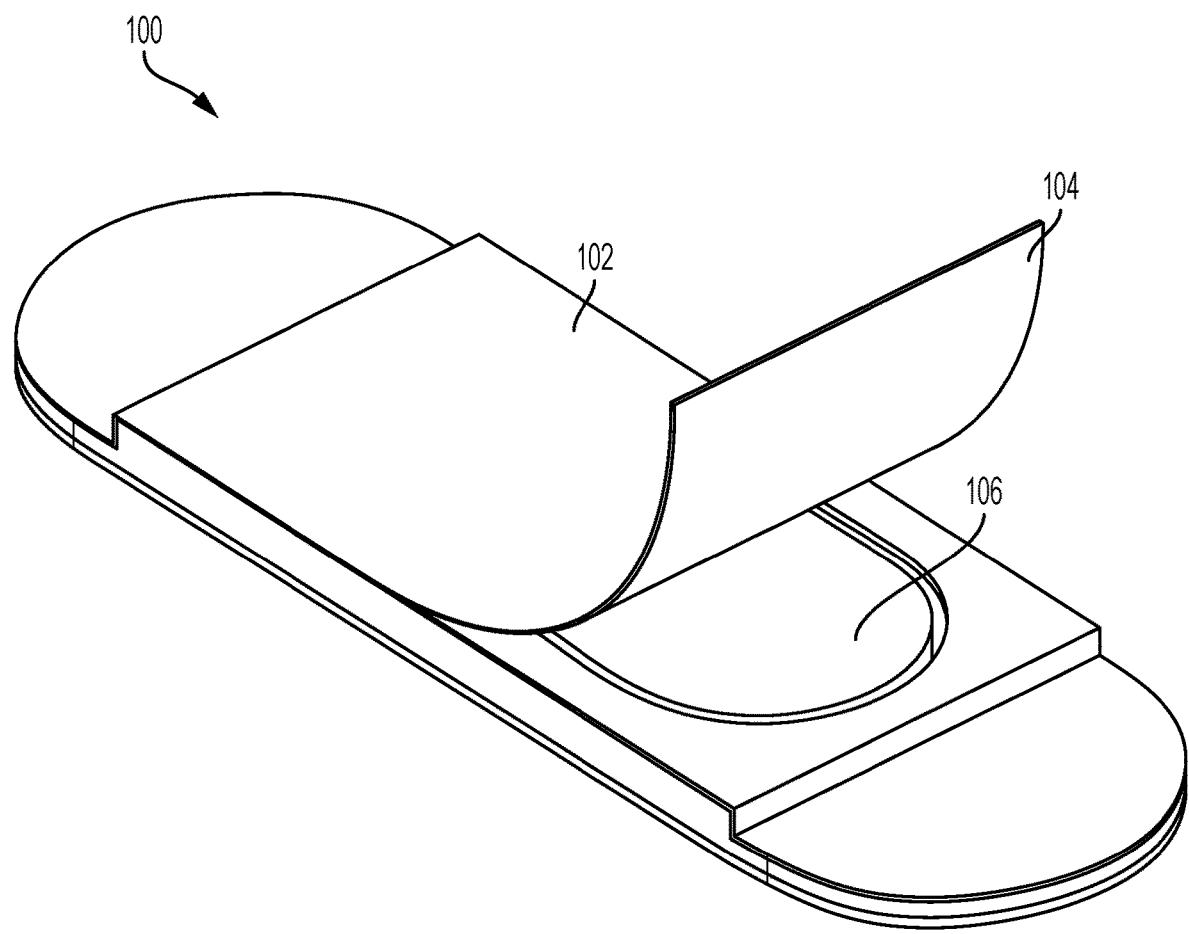
FIG. 1 illustrates a modular wearable sensor in accordance with an embodiment.

FIG. 1 illustrates a modular wearable sensor 100 in accordance with an embodiment. The modular wearable sensor 100 includes a disposable module 102, a cover 104 coupled to the disposable module 102, and a reusable module 106 coupled to the disposable module 102. In one embodiment, after the reusable module 106 is coupled to the disposable module 102, the cover 104 is coupled to the disposable module 102 to enclose the reusable module 106 within the disposable module 102.

One of ordinary skill in the art readily recognizes that the cover 104 can be a variety of types of covers including but not limited to a flexible cover, a bendable cover, a stiff cover, and an elastic cover and that would be within the spirit and scope of the present invention. Additionally, one of ordinary skill in the art readily recognizes that the cover 104 can be coupled to the disposable module 102 utilizing a variety of coupling mechanism including but not limited to an adhesive and a clip and that would be within the spirit and scope of the present invention.

In one embodiment, the cover 104 is coupled to a top surface of the disposable module 102. One of ordinary skill in the art readily recognizes that the cover 104 can be coupled to a variety of surfaces of the disposable module 102 to allow varying coupling orientations of the reusable module 106 to the disposable module 102 including but not limited to a bottom surface and a side surface and that would be within the spirit and scope of the present invention.

In one embodiment, the disposable module 102 includes an outer shell unit that houses various components. The outer shell is soft, flexible, and stretchable to provide optimum wear comfort when attached to the body of a user. Additionally, the outer shell is waterproof and sealed so that a user can come in contact with water without having to detach the modular wearable sensor 100. The various components housed within the disposable module 102 can include but are not limited to a cover, foam layers, at least one power source, a flexible printed circuit board (PCB) including electrical components such as a connector, a small sensor, and a thermistor, electrode contacts to couple to electrodes, and an adhesive layer.

In one embodiment, the reusable module 106 includes an outer shell unit that houses various components including critical electronics. The outer shell is hard and rigid to protect the critical electronics. The various components including critical electronics housed within the reusable module 106 can include but are not limited to a connector, an antenna, a microcontroller, a sensor, a microelectromechanical system (MEMS), and a wireless transceiver. The reusable module 106 can be de-attached from the disposable module 102 via the connectors for re-use with another disposable module and/or wireless sensor device that includes a related connector.

One of ordinary skill in the art readily recognizes that the at least one power source can be a variety of device types including but not limited to a coin battery, a button battery, a flexible battery, and an energy harvesting unit and that would be within the spirit and scope of the present invention. Additionally, one of ordinary skill in the art readily recognizes that the various other components housed within both the disposable module 102 and the reusable module 106 can vary in device type and material and that would be within the spirit and scope of the present invention.

Figure 2:
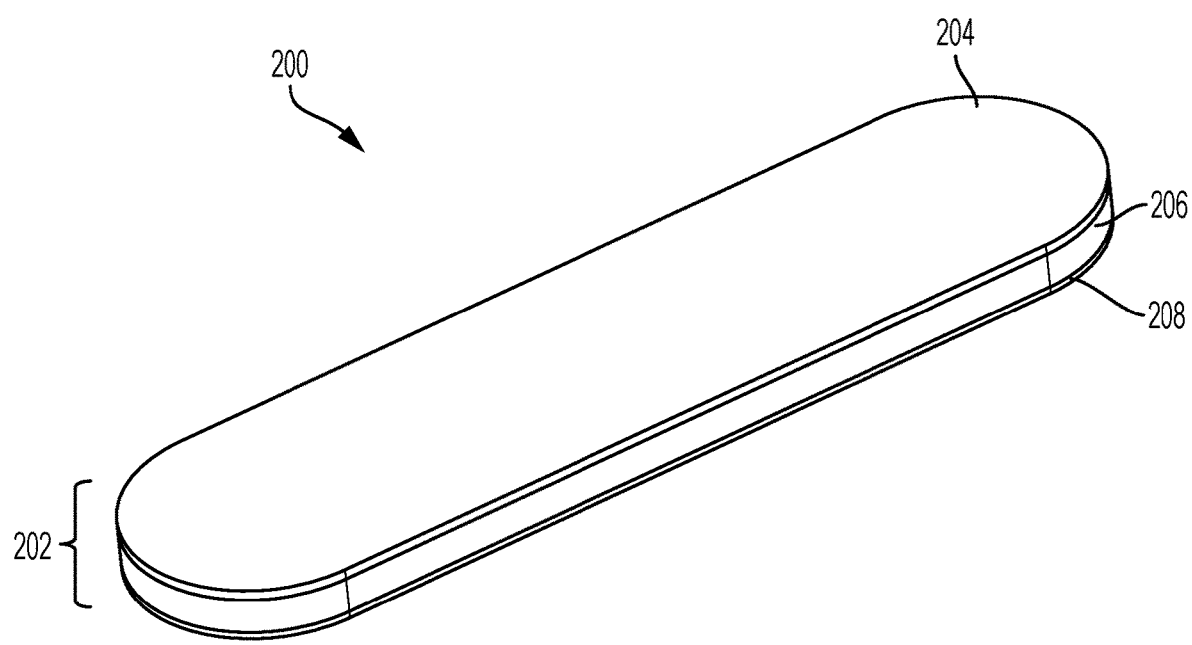
FIG. 2 illustrates an external view of a disposable module in accordance with an embodiment.

FIG. 2 illustrates an external view of a disposable module 200 in accordance with an embodiment. The disposable module 200 includes an outer shell 202. The outer shell 202 includes a top surface 204, a middle layer 206, and a bottom surface 208. In one embodiment, the outer shell 202 has a thickness variation across the top surface 204. One of ordinary skill in the art readily recognizes that the thickness variation across the top surface 204 can be a variety of thickness patterns including but not limited to a center portion of the top surface 204 being thicker than both end portions of the top surface 204 and that would be within the spirit and scope of the present invention.

Figure 3:
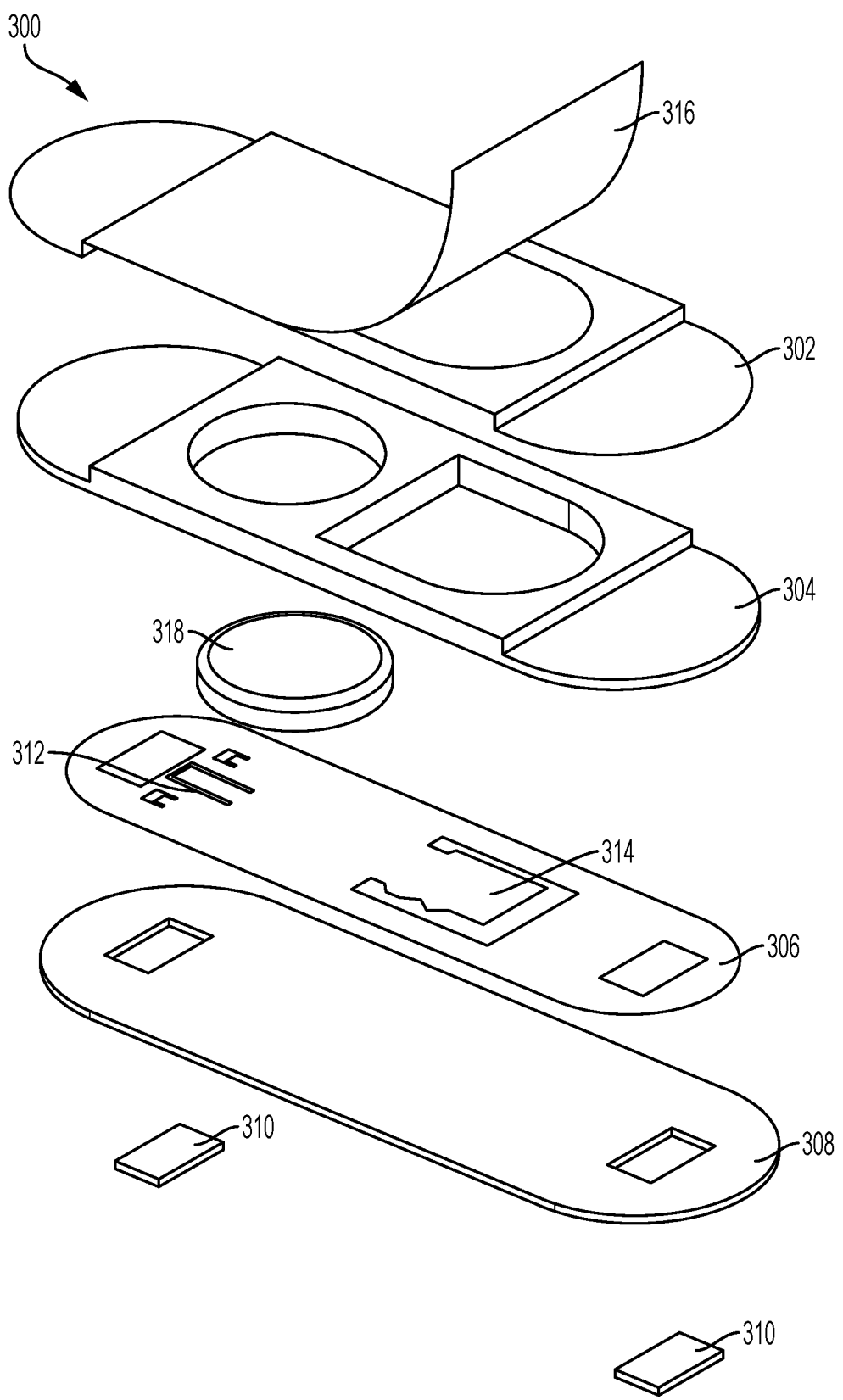
FIG. 3 illustrates an exploded view of a disposable module in accordance with an embodiment.

FIG. 3 illustrates an exploded view of a disposable module 300 in accordance with an embodiment. The disposable module 300 includes a top cover layer 302, a top foam layer 304 coupled to the top cover layer 302, a flexible PCB 306 coupled to the top foam layer 304, a bottom foam layer 308 coupled to the flexible PCB 306, and at least two electrodes 310 coupled to the flexible PCB 306. The flexible PCB 306 enables the disposable module 300 to conform and to adhere to a user's movements. In the disposable module 300, the flexible PCB 306 includes an electrical component unit 312 including but not limited to a thermistor and a first connector unit 314 that enables the coupling of the disposable module 300 to the reusable module 106.

In one embodiment, the bottom foam layer 310 is a double adhesive layer so that it adheres to the flexible PCB 306 and to a user at the same time. One of ordinary skill in the art readily recognizes that the at least two electrodes 310 can measure a variety of health related values including but not limited to ECG and respiratory rates and that would be within the spirit and scope of the present invention.

In one embodiment, the top cover layer 302 and the top foam layer 304 each have an opening to allow for the insertion and coupling of the reusable module 106. The opening of the top cover layer 302 is covered by an adjustable cover 316 to protect the reusable module 106 once inserted and coupled to the first connector unit 314. One of ordinary skill in the art readily recognizes that each of the openings of the top cover layer 302 and the top foam layer 304 can be similarly shaped or different as long as they are shaped in accordance with the shape of the reusable module 106 and that would be within the spirit and scope of the present invention.

In one embodiment, the top foam layer 304 has another opening for the insertion and coupling of a battery 318. The battery 318 is coupled to the flexible PCB 306 to power both the electrical component unit 312 of the flexible PCB 306 and the reusable module 106 through the connector unit 314. In another embodiment, a waterproof and breathable battery cover is utilized to protect the battery 318. One of ordinary skill in the art readily recognizes that the disposable module 300 can include a variety of power sources including but not limited to a single battery and multiple batteries and that would be within the spirit and scope of the present invention.

In one embodiment, the flexible PCB 306 and the bottom foam layer 308 each have two openings to allow for the coupling of the at least two electrodes 310 to the electrode contacts of the flexible PCB 306. In one embodiment, the at least two electrodes 310 are made of an electrolyte, including but not limited to an electrolytic medium or gel (hydrogel), and an electrochemical electrode, including but not limited to a metallic electrode. One of ordinary skill in the art readily recognizes that each of the two openings of the flexible PCB 306 and the bottom foam layer 308 can be similarly shaped or different as long as they are shaped in accordance with the shape of the at least two electrodes 310 and that would be within the spirit and scope of the present invention.

Figure 4:
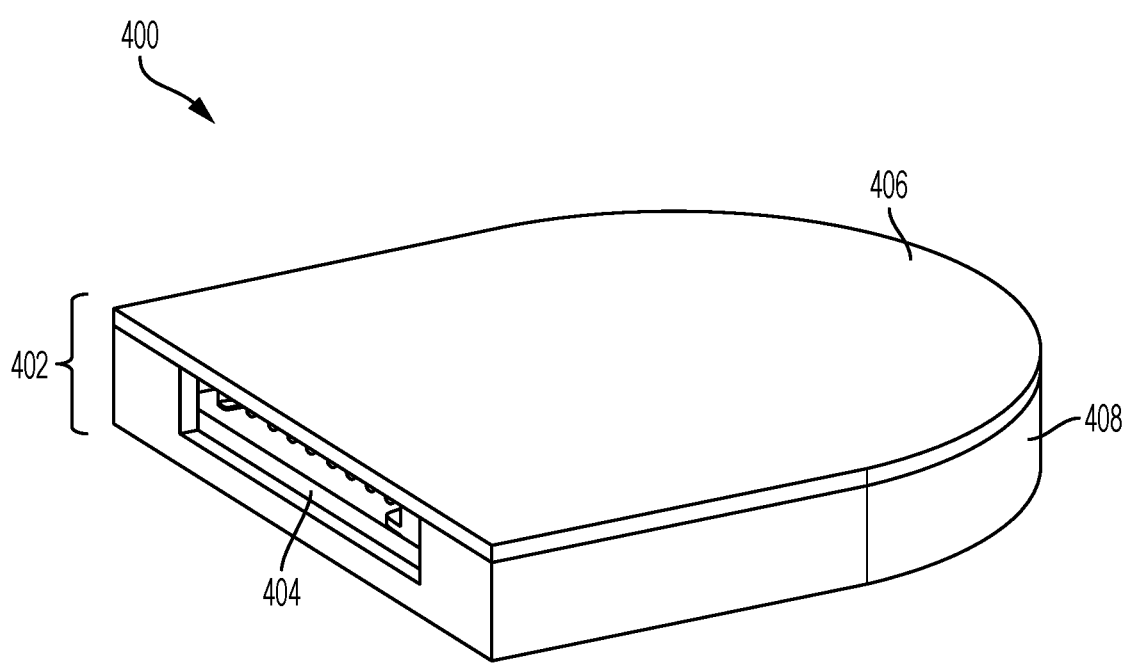
FIG. 4 illustrates an external view of a reusable module in accordance with an embodiment.

FIG. 4 illustrates an external view of a reusable module 400 in accordance with an embodiment. The reusable module 400 includes an outer shell 402 and a connector opening 404 coupled to the outer shell 402. The outer shell 402 includes a top surface 406, a middle layer 408 that houses electrical components, and a bottom surface. In one embodiment, the outer shell 402 is comprised of a hard material to protect the electrical components housed within.

Figure 5:
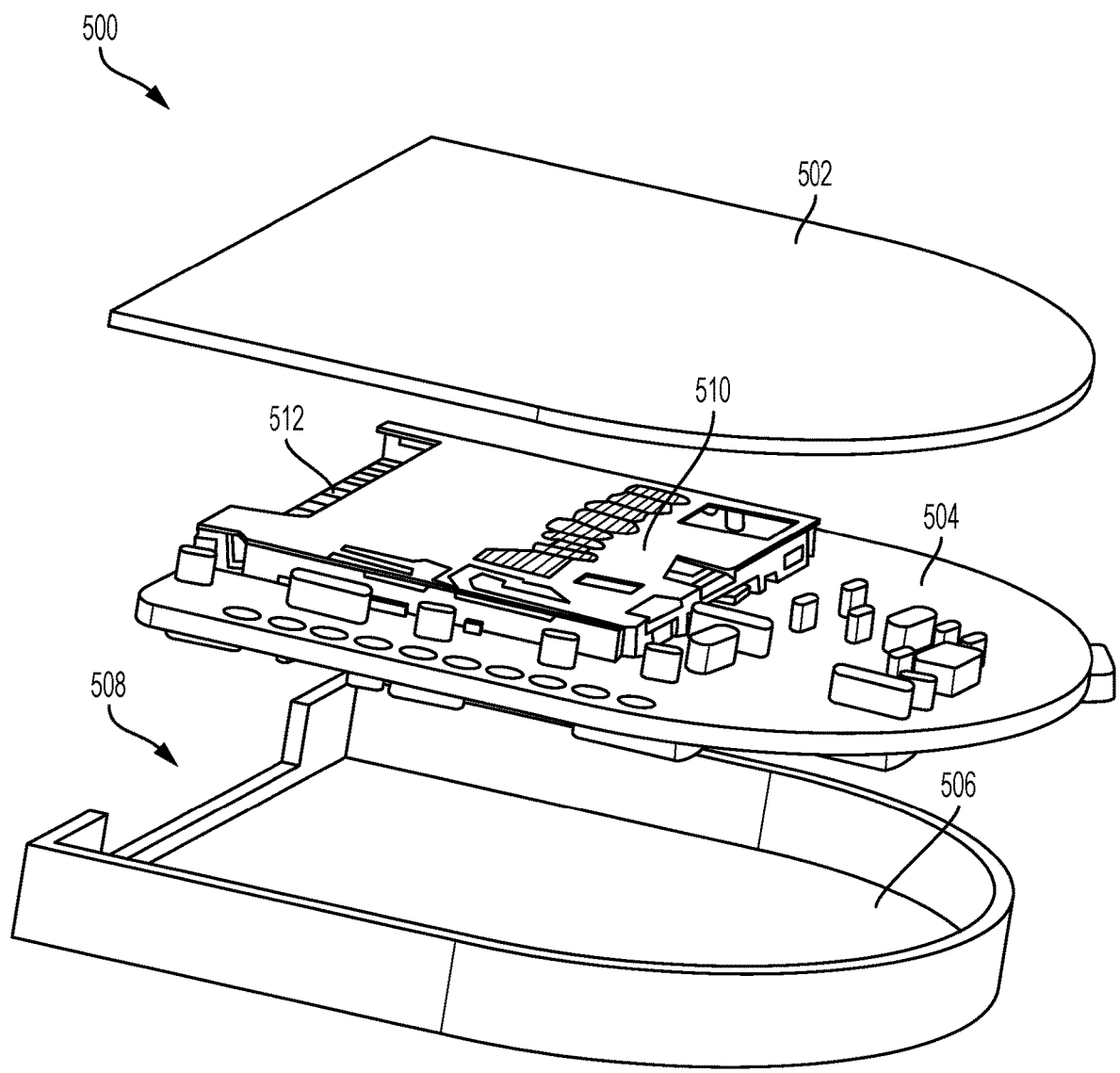
FIG. 5 illustrates an exploded view of a reusable module in accordance with an embodiment.
Figure 6:
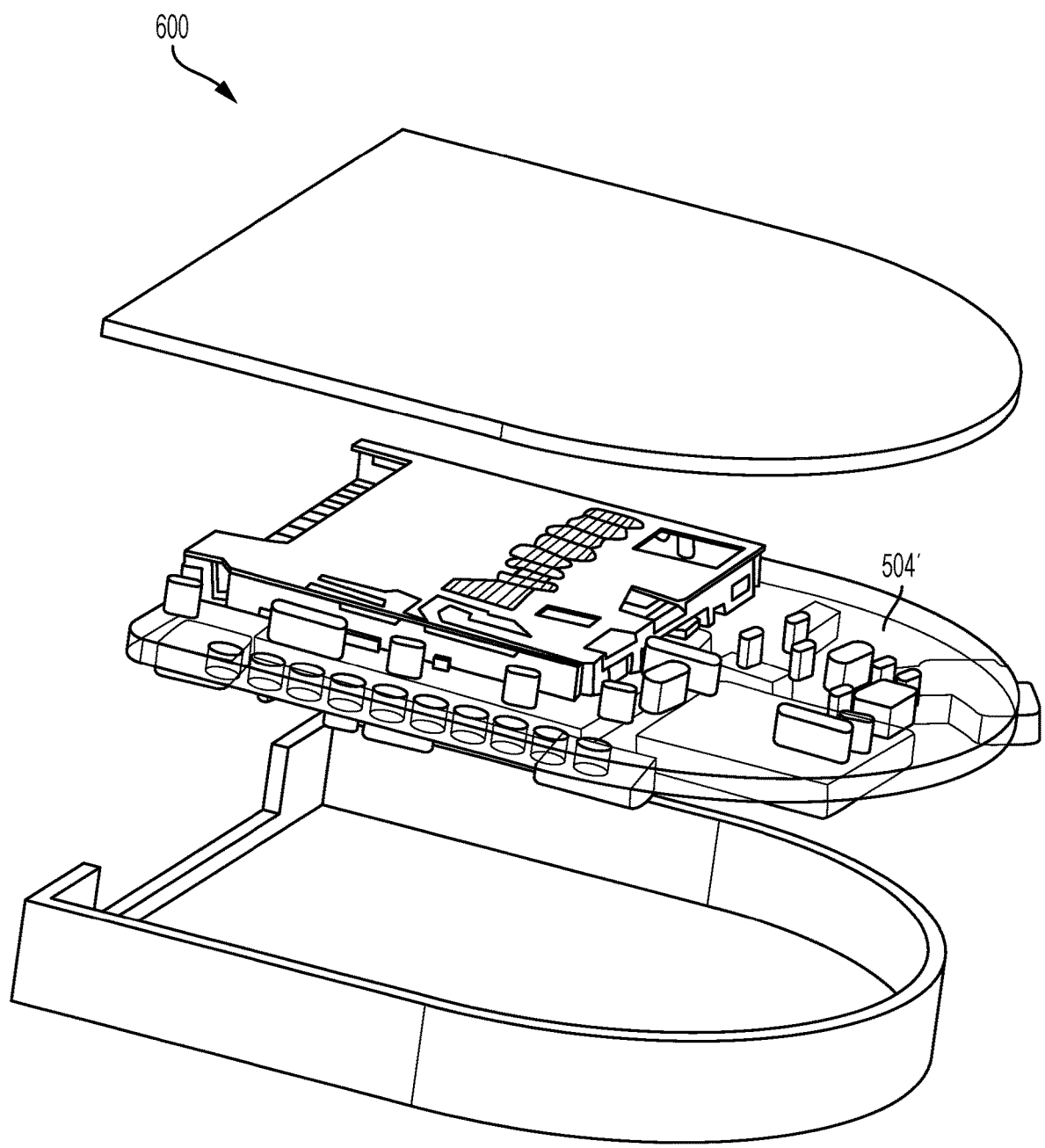
FIG. 6 illustrates an exploded view of a reusable module with a transparent PCB in accordance with an embodiment.

FIG. 5 illustrates an exploded view of a reusable module 500 in accordance with an embodiment. The reusable module 500 includes a top cover layer 502, a bottom cover layer 506 coupled to the top cover layer 502, a PCB 504 coupled between the top cover layer 502 and the bottom cover layer 506, and a connector opening 508 coupled to both the top cover layer 502 and the bottom cover layer 506. The PCB 504 includes an electrical component unit 510 and a second connector unit 512 coupled to the electrical component unit 510 for further monitoring and processing of information collected by the at least two electrodes 310. FIG. 6 illustrates a transparent view 600 of the PCB of the reusable module 500. In the transparent view 600, the PCB 504' is transparent so that components coupled on both sides of the PCB 504' are visible.

Figure 7:
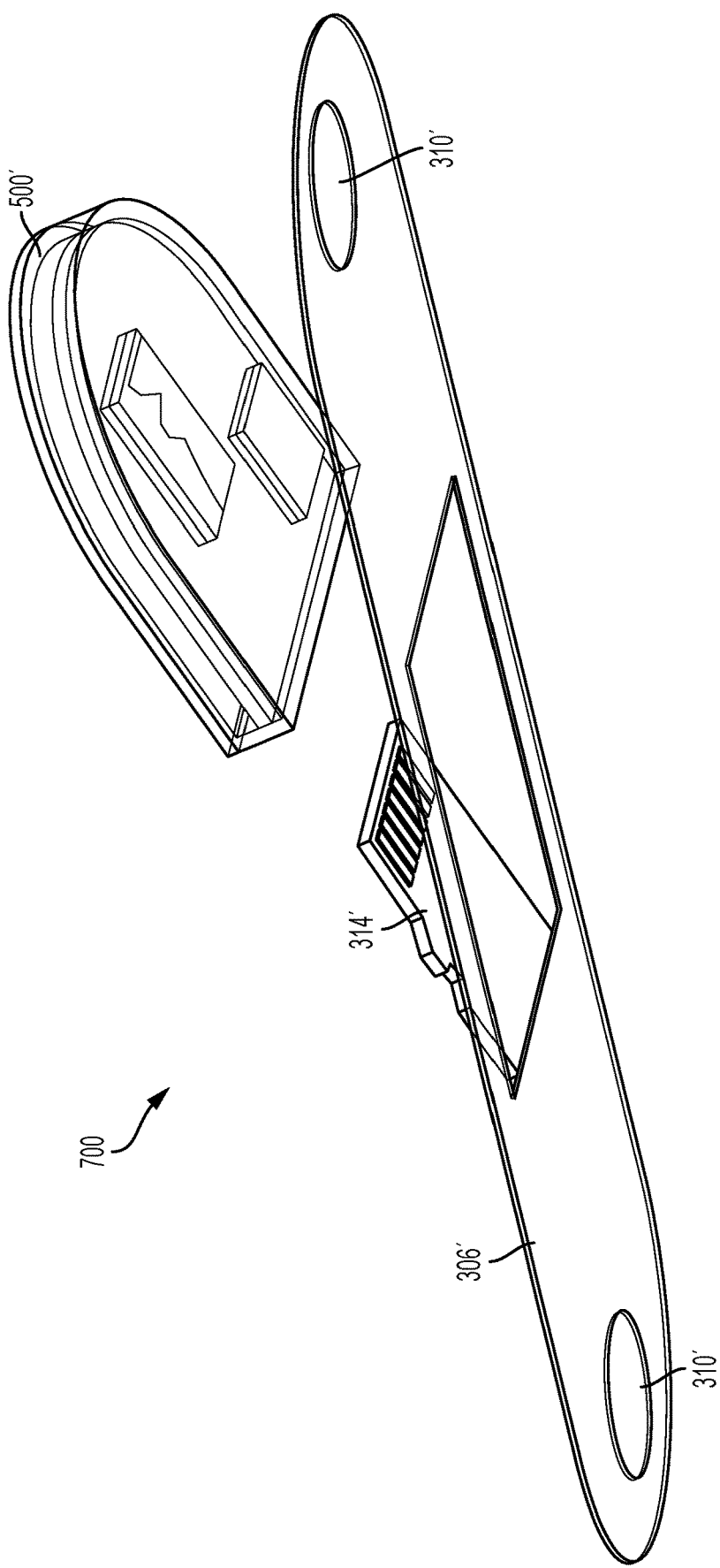
FIG. 7 illustrates a view of the connection between the disposable module and the reusable module in accordance with an embodiment.

The first connector unit 314 of the flexible PCB 306 couples to the second connector unit 512 of the reusable module 500 to provide connectivity between the at least two electrodes 310 and the reusable module 500. The coupling between the first connector unit 314 and the second connector unit 512 enables the modular wearable sensor 100 to monitor health related values of the user for either a continuous period or predetermined time period. FIG. 7 illustrates a view of the connection 700 between the disposable module and the reusable module in accordance with an embodiment. The second connector unit of the reusable module 500' can be coupled to the first connector unit 314' of the flexible PCB 306' to connect the at least two electrodes 310' to the reusable module 500'.

One of ordinary skill in the art readily recognizes that the first connector unit 314 of the flexible PCB 306 within the disposable module 300 and the second connector unit 512 of the PCB 504 within the reusable module 500 can be a variety connector types including but not limited to Secure Digital (SD) card connectors, miniSD card connectors, microSD card connectors, flash memory card connectors, and custom designed connectors and that would be within the spirit and scope of the present invention.

One of ordinary skill in the art readily recognizes that the flexible PCB 306 of the disposable module 300 can include similar electrical components as the PCB 504 of the reusable module 500 and that would be within the spirit and scope of the present invention. In this embodiment, the modular wearable sensor 100 would include only the disposable module 300 that is capable of monitoring health related values of the user, rendering the modular wearable sensor 100 entirely disposable.

As above described, the modular wearable sensor and method provide for a cost-efficient health monitoring device that includes at least one reusable module and at least one disposable module that are capable of decoupling from each other to enable the continuous monitoring of a user. By implementing similar connector units within both the disposable module and the reusable module of the modular wearable sensor, the reusable module can be decoupled from the disposable module. Complex and costly electrical components for the health monitoring and processing of a user's data can be housed within the reusable module portion so that when the disposable module is discarded, higher monitoring costs do not result.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A wearable sensor, comprising:
a first module, wherein the first module comprises a top layer structure, a printed circuit board (PCB) layer, and a bottom layer, and
a second module coupled to the first module, wherein the first module is disposable and the second module is reusable;
wherein the PCB layer is selected from the group consisting of a soft PCB, a flexible PCB, and a stretchable PCB to provide wear comfort,
and wherein the bottom layer comprises a double adhesive layer that adheres to the PCB layer on one side and is capable of adhering to a user on the other side, wherein the bottom layer includes at least two openings to house at least two electrodes capable of monitoring the user, wherein each of the at least two openings houses one electrode; and
wherein the top layer structure comprises a top cover layer and a top foam layer each having an opening allowing for the insertion of the second module, and
wherein the opening of the top cover layer is covered by an adjustable cover to protect the reusable module once inserted.

2. The wearable sensor of claim 1, wherein the PCB layer is coupled between the top layer structure and the bottom layer.

3. The wearable sensor of claim 1, further comprising:
at least one power source coupled to the first module.

4. The wearable sensor of claim 3, wherein the first module further comprises a first outer shell that houses the PCB layer, the top layer structure and the bottom layer coupled to the PCB layer, wherein the top layer structure includes another opening for housing the at least one power source.

5. The wearable sensor of claim 4, wherein the second module is coupled to the first module via the second opening, wherein the second module comprises a second outer shell that houses another PCB layer.

6. The wearable sensor of claim 5, wherein the second outer shell comprises a second top cover, a bottom cover coupled to the second top cover, and a connector opening coupled to the bottom cover, wherein the another PCB layer is coupled between the second top cover and the bottom cover.

7. The wearable sensor of claim 5, wherein the second outer shell is selected from the group consisting of two horizontally coupled pieces and a conformal coating form.

8. The wearable sensor of claim 3, wherein the at least one power source is selected from the group consisting of a rechargeable battery, a coin battery, a button battery, a flexible battery, an energy harvesting unit, and a solar cell, further wherein the at least one power source is coupled to the first module via the PCB layer.

9. The wearable sensor of claim 5, wherein the PCB layer comprises a first connector coupled to a stiffener.

10. The wearable sensor of claim 1, wherein the PCB layer comprises a first electrical component that is selected from the group consisting of a small sensor and a thermistor.

11. The wearable sensor of claim 9, wherein the another PCB layer comprises a second electrical component that is selected from the group consisting of a second connector, an antenna, a microcontroller, a microelectromechanical system (MEMS), and a wireless transceiver.

12. The wearable sensor of claim 4, wherein a center portion of the first top cover is thicker than peripheral portions of the first top cover.

13. The wearable sensor of claim 1, wherein the double adhesive layer of the bottom layer is a hydrogel layer.

14. The wearable sensor of claim 11, further comprising the second connector, wherein the second connector is coupled to the first connector via the second opening of the top layer.

15. The wearable sensor of claim 9, wherein the first connector is selected from the group consisting of a standard MicroSD card form factor and a custom designed card form factor.

16. A method for providing a wearable sensor, comprising:
   providing a first module, wherein the first module comprises a top layer structure, a printed circuit board (PCB) layer, and a bottom layer, coupling a second module to the first module, wherein the first module is disposable and the second module is reusable;
   wherein the PCB layer is selected from the group consisting of a soft PCB, a flexible PCB, and a stretchable PCB to provide wear comfort, and wherein the bottom layer comprises a double adhesive layer that adheres to the PCB layer on one side and is capable of adhering to a user on the other side, wherein the bottom layer includes at least two openings to house at least two electrodes capable of monitoring the user, wherein each of the at least two openings houses one electrode; and
   wherein the top layer structure comprises a top cover layer and a top foam layer each having an opening allowing for the insertion of the second module, and
   wherein the opening of the top cover layer is covered by an adjustable cover to protect the reusable module once inserted.

17. The method of claim 16, further comprising:
   coupling at least one power source to the first module.

18. The method of claim 17, wherein the first module further comprises a first outer shell that houses the PCB layer, the top layer structure and the bottom layer coupled to the PCB layer, wherein the top layer structure includes another opening for housing the at least one power source.

19. The method of claim 18, wherein the second module is coupled to the first module via the second opening, wherein the second module comprises a second outer shell that houses another PCB layer.

* * * * *